(12) United States Patent
Wanner

(10) Patent No.: US 6,627,160 B2
(45) Date of Patent: Sep. 30, 2003

(54) MULTIPLE CHANNEL PIPETTING DEVICE

(75) Inventor: Jurgen Wanner, Wertheim (DE)

(73) Assignee: Brand GmbH + Co. KG

( * ) Notice: Subject to any disclaimer, the term of this patent is extended or adjusted under 35 U.S.C. 154(b) by 351 days.

(21) Appl. No.: 09/811,820

(22) Filed: Mar. 20, 2001

(65) Prior Publication Data

US 2001/0043885 A1 Nov. 22, 2001

(30) Foreign Application Priority Data

Mar. 20, 2000 (DE) .......................................... 100 13 511

(51) Int. Cl.⁷ .............................. B01L 3/02; G01N 1/14
(52) U.S. Cl. ..................... 422/100; 73/863.32; 73/864; 73/864.01; 73/864.11; 73/864.13; 73/864.14; 73/864.16; 73/864.17; 73/863.25
(58) Field of Search ....................... 422/100; 73/863.32, 73/864, 864.01, 864.11, 864.16, 864.13, 864.14, 864.17, 863.25

(56) References Cited

U.S. PATENT DOCUMENTS

| | | | |
|---|---|---|---|
| 3,732,735 A | | 5/1973 | Cohen |
| 3,855,868 A | | 12/1974 | Sudvaniemi |
| 4,444,062 A | * | 4/1984 | Bennett et al. ........... 73/863.32 |
| 4,824,642 A | * | 4/1989 | Lyman et al. ................ 422/100 |
| 5,104,624 A | | 4/1992 | Labriola |
| 5,364,596 A | | 11/1994 | Magnussen, Jr. et al. |
| 5,525,302 A | * | 6/1996 | Astle ........................... 422/100 |
| 5,736,105 A | * | 4/1998 | Astle ........................... 422/100 |
| 5,770,160 A | * | 6/1998 | Smith et al. ................. 422/100 |
| 5,874,048 A | | 2/1999 | Seto et al. |
| 6,019,004 A | * | 2/2000 | Conley et al. ........... 73/864.16 |
| 6,143,252 A | * | 11/2000 | Haxo et al. ................. 422/131 |
| 6,258,324 B1 | * | 7/2001 | Yiu ............................. 422/100 |
| 6,365,110 B1 | * | 4/2002 | Rainin et al. ............... 422/100 |
| 6,540,964 B2 | * | 4/2003 | Kohrmann et al. ......... 422/100 |
| 2002/0081234 A1 | * | 6/2002 | Homberg et al. ........... 422/100 |
| 2002/0086440 A1 | * | 7/2002 | Lehtinen et al. ............ 436/180 |

FOREIGN PATENT DOCUMENTS

| | | |
|---|---|---|
| DE | 69 43 120 | 11/1968 |
| DE | 1 291 142 | 3/1969 |
| DE | 29 21 443 | 12/1979 |
| DE | 202 397 | 9/1983 |
| DE | 283 779 A5 | 10/1990 |
| EP | 0 041 318 | 12/1981 |
| EP | 0 348 612 A2 | 1/1990 |
| EP | 0 701 865 A1 | 3/1996 |

* cited by examiner

*Primary Examiner*—Jill Warden
*Assistant Examiner*—Brian R. Gordon
(74) *Attorney, Agent, or Firm*—Nixon Peabody LLP; David S. Safran

(57) ABSTRACT

A multiple channel pipetting device and pipette shaft, in which each pipette shaft has a circumferential seal receptacle inside, at its upper end in which the circumferential plunger seal is positioned and in which the circumferential plunger seal, at least in the case of a pulled back pipette plunger, definitely remains in the seal receptacle when the pipetted shaft is removed from the shaft carrier.

28 Claims, 4 Drawing Sheets

MULTIPLE CHANNEL PIPETTING DEVICE

SUMMARY OF THE INVENTION

1. Field of the Invention

The object of the invention is a multiple channel pipetting device as well as an exchangeable pipette shaft for a pipetting device.

2. Description of Related Art

The known multiple channel pipetting device, on which the invention is based (U.S. Pat. No. 3,855,868) is suitable for small stand distances of individual, neighboring pipette tips, in particular, for the low stand distances required in so-called micro titration stands. In order to be able to implement these small stand distances, the pipette shafts of this multiple channel pipetting device are removably inserted in the inset shaft receptacles of the shaft carrier. Specifically, the pipette shafts are provided with external threading on the upper end which can be screwed into the internal threading in the shaft receptacle.

The multiple channel pipetting device of the prior art is designed as an air buffer pipetting device, wherein the pipette tips, for ingesting liquid, are pushed onto the tip holder of the pipette shaft. The pipette holders are so smoothly designed on the surface, that the pipette tips can be directly sealingly pushed on. This results, however, in certain demands on the pipette tips.

Being an air buffer pipetting device, the above-mentioned multiple channel pipetting device naturally needs a circular plunger seal for the pipette plunger. Here, in each case, this is arranged on the upper end of the plunger receptacle facing the plunger carrier in the shaft carrier and is designed as a circumferential seal of elastomer material, namely an O-ring. The air volume relevant when pipetting is thus formed, on the one hand, by the cylinder in the pipette shaft, but moreover, also by the volume of the plunger receptacle between the pipette shaft and the plunger seal. The pipette shaft must then be sealingly screwed into the shaft receptacle in the shaft carrier. This requires special materials or an additional seal at this position.

Should just one channel of the above-mentioned multiple channel pipetting device have a leak, the entire pipetting device has to be taken apart because it is necessary to then be able to reach the plunger seal in the shaft carrier. Normally, it is not known if the leak comes from the plunger seal, from the seal between the pipette shaft and the shaft receptacle or from the seal between the pipette tip and the tip holder. Maintenance is work intensive and expensive.

Attaching a pipette shaft by means of a screw-cap has been known for decades (U.S. Pat. No. 3,732,735, DD 283 779 A) in respect to one channel pipetting devices. The thus existing undercut on the pipette shaft is used to provide a circular seal receptacle on the upper end of the pipette shaft in which the plunger seal is arranged. The plunger seal is affixed in this plunger receptacle by an affixing element which is provided with external threading to be screwed into the internal threading of the screw-cap. This construction is comparably work intensive and takes up so much space in the radial direction due to the screw-cap, that it can not be seen as suitable for the required stand measurements, in particular in micro titration stands.

SUMMARY OF THE INVENTION

The object of the teaching is thus, to make the maintenance of the known multiple channel pipetting device described above, which is also determined and suitable for low stand measurements, more user-friendly.

The object described above is met by a multiple channel pipetting device according to the invention in which each pipette shaft has a circumferential seal receptacle inside, at its upper end in which the circumferential plunger seal is positioned and in which the circumferential plunger seal, at least in the case of a pulled back pipette plunger, definitely remains in the seal receptacle when the pipette shaft is removed from the shaft carrier.

It has been recognized that it is practical for the maintenance of a multiple channel pipetting device of the sort described here, that all of the seals are provided on the pipette shaft. Should, namely, the plunger seal for the pipette plunger also be arranged in the pipette shaft, an additional seal between the pipette shaft and the shaft carrier is not needed because the air volume is confined to the pipette shaft. In this case, it comes to the simple measure, in the case of a leak, that only the pipette shaft has to be taken apart and exchanged without having to pay attention to which of the two seals—plunger seal or pipette tip seal—is responsible for the leak. Nothing has to be completely taken apart or exchanged from the pipetting device, the problem is corrected by merely exchanging the pipette shaft.

The invention is based on the realization that above-explained concept can be achieved even with a multiple channel pipetting device where the shaft receptacles are inserted in the shaft carrier.

Moreover, the invention covers a pipette shaft for such a pipetting device, too.

In the following, the invention is explained more precisely with a drawing presenting merely one preferred embodiment.

SUMMARY OF THE INVENTION

DETAILED DESCRIPTION OF THE INVENTION

Figure 1:
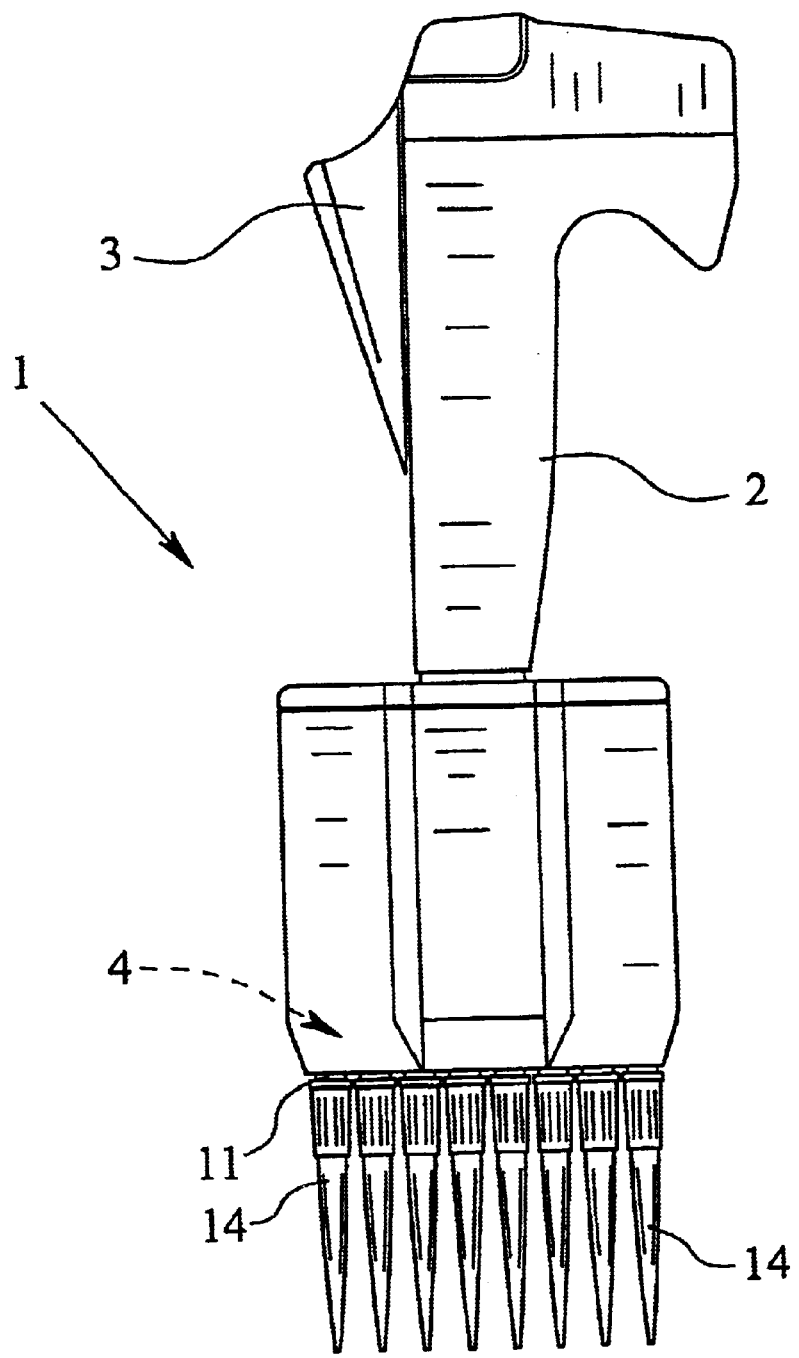
FIG. 1 is a perspective view of an example of a multiple channel pipetting device of the present application.

First, FIG. 1 shows, in general, a multiple channel pipetting device as it is used as a "transfer pipette." With such a multiple channel pipetting device, it is possible to ingest one and the same amount of liquid from a plurality of reaction vessels which are, for example, arranged grid-like on a micro-titration stand and transport it to another place or bring it from another place to the reaction vessels. This practice is known from the prior art and is sufficiently mentioned in the literature reference so that it may be referred to.

The general multiple channel pipetting device shown in FIG. 1 has a housing 1 with a gripping handle 2 on which an actuating button 3 for pipetting is found. A shaft carrier 4 on the housing 1 has multiple pipette shafts 11 on the lower part, which can each exchangably carry a pipette tip 14.

FIG. 2 shows the internal construction of a multiple channel pipetting device according to the invention. A transversely arranged shaft carrier 4 and a moveable plunger carrier 5 also transversely arranged above the shaft carrier 4 are found in the housing 1. The vertical movement of the plunger carrier 5 relative to the shaft carrier 4 is triggered by actuating the actuating button 3 mentioned in connection with FIG. 1.

A pipette plunger 7, positioned on the plunger carrier 5, enters into each of multiple plunger receptacles 6 found in the shaft carrier 4. In the embodiment shown, each pipette plunger 7 is resiliently positioned on the plunger carrier 5 by means of a spring element 8 and a threaded mounting 9 which do not need to be discussed in detail here.

The number of plunger receptacles 6 in the shaft carrier 4 corresponds to the number of shaft receptacles 10 extending from the plunger receptacles 6. The shaft receptacles 10 are inserted into the shaft carrier 4 on the side opposite the plunger receptacles 6. A pipette tip 14 is removably pushed into each of the shaft receptacles 10 in FIG. 2a.

Each pipette shaft 11 has a cylinder 12 adapted for movably receiving the pipette plunger 7, and a tip holder 13 on the lower end for mounting a pipette tip 14, shown in mounted position in FIG. 1. An ejection channel 15 is provided in each tip holder 13 for the air or corresponding gas of the air buffer volume.

In order to be able to precisely pipette by movement of each pipette plunger 7 by means of the air buffer, the pipette plunger 7 must be perfectly sealed in relation to the cylinder 12. A circumferential plunger seal 16 assigned to each pipette plunger 7 serves this purpose.

Figure 2A:
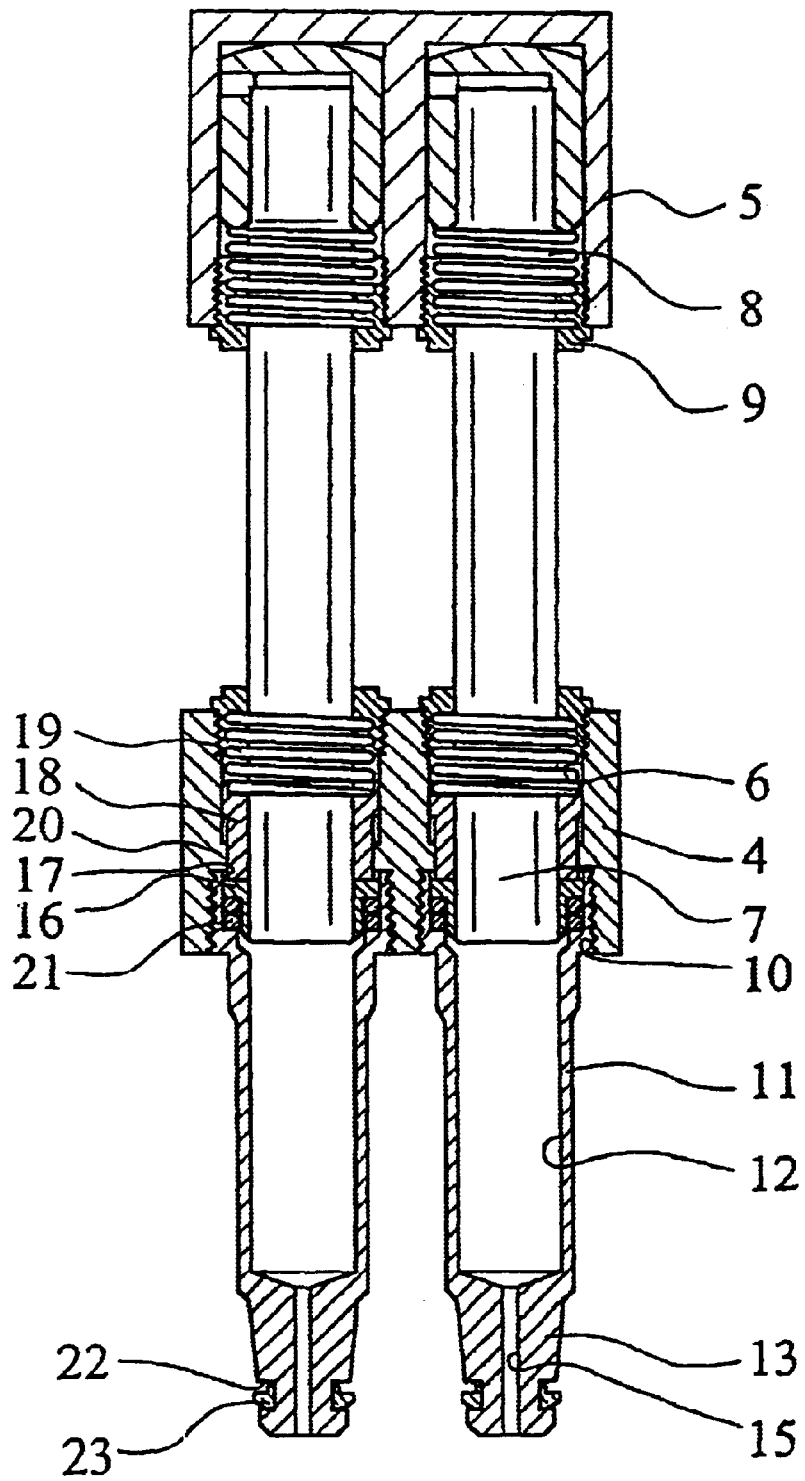
FIG. 2a is a partial, mostly sectional view, of a multiple channel pipetting device according to the invention with two plungers arranged next to one another, assembled in a ready-to-use fashion.

What is important now, is that each pipette shaft 11 has a circumferential seal receptacle 17 on its upper end in which the above-mentioned circumferential plunger seal 16 is arranged. FIG. 2a shows the ready to use pipette shafts 11 mounted on the shaft carrier 4 and also screwed into the shaft receptacle 10. It can be seen that the pipette plungers 7 just dip down into the plunger seals 16 on the upper ends of the pipette shafts 11.

Figure 2B:
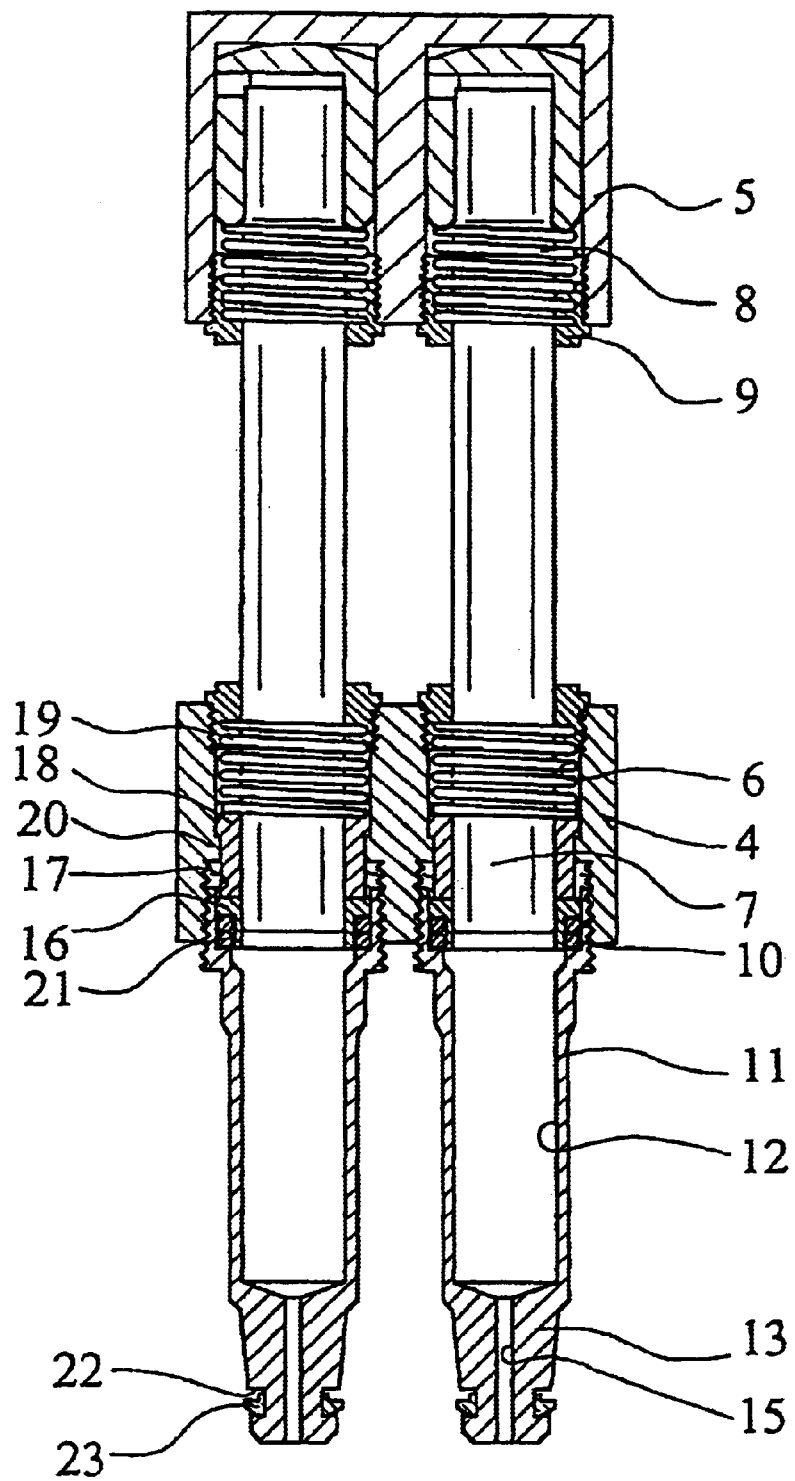
FIG. 2b is a view corresponding to that of FIG. 2a, but with the pipette shafts partially unscrewed.
Figure 2C:
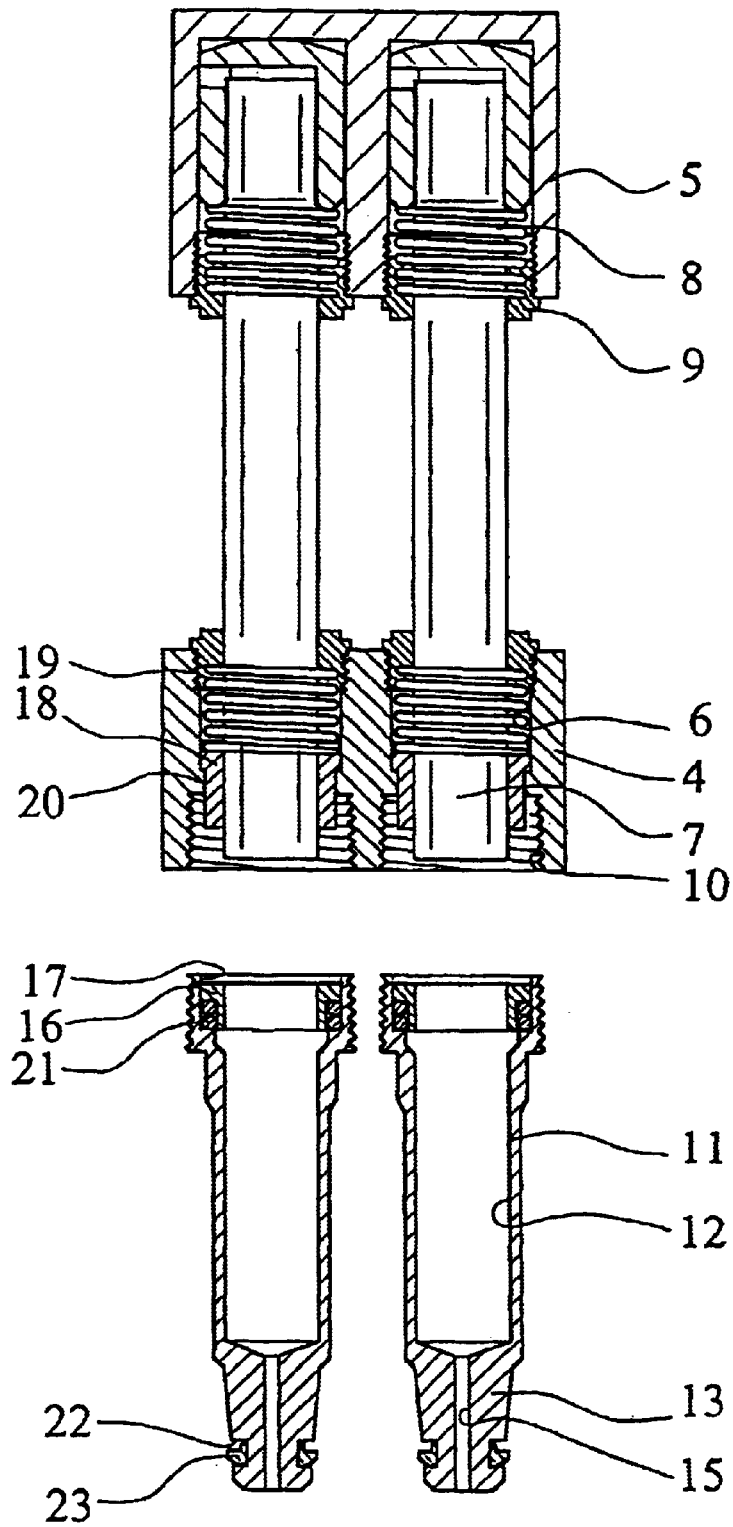
FIG. 2c is a view corresponding to that of FIG. 2a, but with the pipette shafts completely unscrewed.

FIG. 2c shows the arrangement of FIG. 2a, however, with removed, unscrewed pipette shafts 11. It can be seen that the circular plunger seal 16 remains in the seal receptacle 17 in the pipette shaft 11 when the pipette shaft 11 is removed from the shaft carrier 4. This is definitely correct in the arrangement in which the pipette plunger 7 is found in the highest position, the pulled-back position.

The main advantage of the invention can be seen in FIG. 2c. All seal areas including the plunger seal 16 are positioned on the pipette shaft 11 so that possibly occurring sealing problems can be taken care of, in any case, by simply exchanging the pipette shaft 11.

Now, a method could be used for affixing the plunger seal 16 onto the pipette shaft 11 which is known from the prior art of single channel pipetting devices and was mentioned above. For this, the plunger seal 16 could be affixed by means of an affixing element, in particular, a spring ring, a screw-in ring or the like. That would additionally require special measures on the seal receptacle 17 of the pipette shaft 11, which moreover could aggravate the insertion of the plunger seal 16 in the seal receptacle 17.

According to the preferred teaching of the invention, a shown in FIGS. 2a–2c, a stripping ring 18 is axially movably arranged in each plunger receptacle 6 in the shaft carrier 4 on the transition of the shaft receptacle 10. The stripping ring 18 is biased downward in the direction of the shaft receptacle 10 by means of a spring element 19. In the case of a mounted pipette shaft 11, the stripping ring 18 affixes the plunger seal 16 in the seal receptacle 17. It is possible that the stripping ring 18 may be pushed out of the shaft receptacle 10 by the spring element 19 when removing the pipette shaft 11. It is thus provided, in the illustrated embodiment, that an abutment 20 is arranged in the stripping ring 18 in the lower part of each plunger receptacle 6 in the shaft carrier 4 against which the stripping ring 18 is biased by means of the spring element 19. With the construction shown, the plunger seal 16 can held in the seal receptacle 17 in the pipette shaft 11 by a friction fit only without any problems. This is very practical for the equipment of the pipette shaft 11 with the plunger seal 16.

In FIG. 2b, the respective pipette shaft 11 is already mostly unscrewed in a downward direction. The stripping ring 18 is pushed downward under effect of spring tension of the spring element 19 and lies against the abutment 20 in FIG. 2b. When the pipette plunger 7 is completely pulled back, it only dips into the plunger seal 16 with just the tip. The friction fit of the plunger seal 16 in the seal receptacle 17 in the pipette shaft 11 is now sufficient by itself to hold the plunger seal 16 in the pipette shaft 11. The pipette shaft 11 can now be completely unscrewed without difficulties, the final state being shown in FIG. 2c. The stripping ring 18 does not move further in the transition from FIG. 2b to FIG. 2c, since it already rests against the abutment 20.

There are naturally many variations in the prior art for the embodiment of the plunger seal 16. An embodiment of the multiple channel pipetting device in this form has proven to be useful for its high exactness in pipetting which is required in many cases in that the plunger seal 16 is designed as a sealing jacket, particularly of PTFE material or another slidable material and is radially biased, preferably by means of an elastomer seal 21, in particular an O-ring. In the embodiment shown, two elastomer seals 21 made of PTFE are provided as back-up for the plunger seal 16. The sealing jacket which forms the plunger seal 16 also, incidentally, has a circumferential contact surface for the stripping ring 18, so that a constant, perfect force transmission takes place.

The spring element 19 has the further function of biasing the plastic parts relative to one another in the shaft carrier 4 and of keeping the pipetting device biased over the entire temperature range of the application. This is especially important when treating by autoclave and is naturally realized primarily by a metallic spring element 19.

The spring element 19 in connection with the stripping ring 18 radially stretches the elastomer seal 21 outward to the seal receptacle 17 via axial pressure. In this manner, the spring element 19 also creates a radially outward seal so that any intake of air into the pipette shaft 11 from outside is prevented.

It has already been indicated above, that the insertion of the pipette shaft 11 into the inset shaft receptacle 10, according to the invention, is implemented in the embodiment in that the pipette shaft 11 is screwed into the shaft receptacle 10. In this respect, there are many alternatives, in particular, a bayonet attachment comes into consideration as well.

The shown and insofar preferred embodiment further shows a particular embodiment of the pipette shaft 11 in the tip holder 13. While the prior art on which the invention is based implements merely a contact seal between the pipette tip 14 and the pipette shaft 11 on the tip holder 13, it is provided according to the teaching of the invention that each pipette shaft 11 has a circular receiver 22 on the tip holder 13 for a tip seal 23. This allows for the application of different material for the pipette tips 14 or for larger irregularities on the inside of the pipette tip 14. The embodiment shown further distinguishes itself in that the tip seal 23 is designed as a V-shaped lip seal of elastomer.

In total, for the pipette shafts 11 of the multiple channel pipetting device according to the invention, a plastic material is particularly useful. For particular applications, other materials, such as glass, come into consideration. For many applications, the materials of the multiple channel pipetting device should be temperature resistant for temperatures occurring during sterilization, in particular steam sterilization, at least in the areas of pipette plungers 7, pipette shafts 11 and pipette tips 14.

In addition to the multiple channel pipetting device, a pipette shaft for a pipetting device with the corresponding, already mentioned features is also within the scope of the of the invention.

What is claimed is:

1. Multiple channel pipetting device, comprising:
   a housing with a transversely arranged shaft carrier and a moveable plunger carrier arranged transversely above the shaft carrier;
   a number of plunger receptacles in the shaft carrier and a corresponding number of pipette plungers positioned on the plunger carrier and inserted in the plunger receptacles;
   a number of shaft receptacles corresponding to the number of plunger receptacles, said shaft receptacles being inserted in the shaft carrier on an opposite side from the plunger carrier and extending from the plunger receptacles; and
   a number of pipette shafts corresponding to the number of shaft receptacles and removably inserted in the shaft receptacles;
      wherein each pipette shaft has a cylinder adapted for the pipette plunger and a tip holder on a lower end with an ejection channel arranged therein;
      wherein an outer side of an upper end of each cylinder is adapted for attachment in a respective shaft receptacle;
      wherein a pipette tip is received on each tip holder; and
      wherein each pipette plunger has a circumferential plunger seal which is positioned in a respective circumferential seal receptacle of an inner upper end of each pipette shaft; and
      wherein the circumferential plunger seal is mounted so as to remain in the seal receptacle, at least in the case of a pulled back pipette plunger, when the pipette shaft is removed from the shaft carrier.

2. Pipetting device according to claim 1, further comprising an affixing element for affixing the plunger seal in the seal receptacle.

3. Pipetting device according to claim 2, said affixing element is one of a spring ring and a screw-on ring attached to the pipette shaft.

4. Pipetting device according to claim 1, further comprising a stripping ring axially movably arranged in each plunger receptacle in the shaft carrier on a transition to the shaft receptacle, said stripping ring being biased downward in a direction of the shaft receptacle by a spring element; and wherein the stripping ring affixes the plunger seal in the seal receptacle when the pipette shaft is mounted in the shaft receptacle.

5. Pipetting device according to claim 4, wherein an abutment for the stripping ring is arranged in a lower part of each plunger receptacle in the shaft carrier, toward which the stripping ring is biased by means of the spring element.

6. Pipetting device according to claim 4, wherein the plunger seal is held in the seal receptacle in the pipette shaft by friction coupling.

7. Pipetting device according to claim 1, wherein the plunger seal is a sealing jacket of a low friction material.

8. Pipetting device according to claim 7, wherein the sealing jacket is radially biased by means of an elastomer seal.

9. Pipetting device according to claim 8, wherein the elastomer seal is an O-ring.

10. Pipetting device according to claim 1, wherein each pipette shaft is screwed into the respective shaft receptacle.

11. Pipetting device according to claim 1, wherein each pipette shaft is held in the respective shaft receptacle by a bayonet lock.

12. Pipetting device according to claim 1, wherein each pipette shaft has a circular receiver on the tip holder in which a tip seal for the pipette tip is received.

13. Pipetting device according to claim 12, wherein the tip seal is an elastomer seal.

14. Pipetting device according to claim 13, wherein the tip seal is a V-shaped lip seal of elastomer material.

15. Pipetting device according to claim 1, wherein the pipette shafts are made of a plastic material.

16. Pipette shaft unit for a pipetting device, comprising,
    a pipette shaft;
    a cylinder adapted to receive a pipette plunger; and
    a tip holder on a lower end of the cylinder with an ejection channel arranged therein;
        wherein an outer side of an upper end of the cylinder is adapted for attachment in a shaft receptacle;
        wherein the tip holder is adapted to receive a pipette tip thereon by pushing;
        wherein a circumferential seal receptacle is arranged at an inner side of the upper end of the cylinder; and
        wherein a circumferential plunger seal for the pipette plunger is positioned in said seal receptacle.

17. Pipetting shaft according to claim 16, further comprising an affixing element for affixing the plunger seal in the seal receptacle.

18. Pipetting shaft according to claim 17, wherein said affixing element is one of a spring ring and a screw-on ring attached to the pipette shaft.

19. Pipetting shaft according to claim 16, wherein the plunger seal is held in the seal receptacle in the pipette shaft by friction coupling.

20. Pipetting shaft according to claim 16, wherein the plunger seal is a sealing jacket of a low friction material.

21. Pipetting shaft according to claim 20, wherein the sealing jacket is radially biased by means of an elastomer seal.

22. Pipetting shaft according to claim 21, wherein the elastomer seal is an O-ring.

23. Pipetting shaft according to claim 16, wherein each pipette shaft is screwed into the respective shaft receptacle.

24. Pipetting shaft according to claim 16, wherein each pipette shaft is held in the respective shaft receptacle by a bayonet lock.

25. Pipetting shaft according to claim 16, wherein each pipette shaft has a circular receiver on the tip holder in which a tip seal for the pipette tip is received.

26. Pipetting shaft according to claim 25, wherein the tip seal is an elastomer seal.

27. Pipetting shaft according to claim 25, wherein the tip seal is a V-shaped lip seal of elastomer material.

28. Pipetting shaft according to claim 16, wherein the pipette shafts are made of a plastic material.

* * * * *